(12) United States Patent
Biddell

(10) Patent No.: US 9,409,109 B2
(45) Date of Patent: Aug. 9, 2016

(54) FILTRATION CONTAINER

(75) Inventor: Christopher Biddell, Glos (GB)

(73) Assignee: SARTORIUS STEDIM BIOTECH GMBH, Goettingen (DE)

( * ) Notice: Subject to any disclaimer, the term of this patent is extended or adjusted under 35 U.S.C. 154(b) by 59 days.

(21) Appl. No.: 13/979,971

(22) PCT Filed: Dec. 27, 2011

(86) PCT No.: PCT/EP2011/006576
§ 371 (c)(1),
(2), (4) Date: Jul. 16, 2013

(87) PCT Pub. No.: WO2012/103914
PCT Pub. Date: Aug. 9, 2012

(65) Prior Publication Data
US 2013/0313184 A1    Nov. 28, 2013

(30) Foreign Application Priority Data

Jan. 31, 2011   (DE) ............... 20 2011 002 149 U

(51) Int. Cl.
*B01D 35/30* (2006.01)
*B01L 3/00* (2006.01)
*G01N 1/40* (2006.01)

(52) U.S. Cl.
CPC ............. *B01D 35/30* (2013.01); *B01L 3/5021* (2013.01); *B01L 2300/0681* (2013.01); *G01N 2001/4088* (2013.01)

(58) Field of Classification Search
CPC ........... B01D 35/30; B01L 2300/0681; B01L 3/5021; G01N 2001/4088
See application file for complete search history.

(56) References Cited

U.S. PATENT DOCUMENTS

| 4,722,792 A | 2/1988 | Miyagi et al. |
| 4,769,145 A | 9/1988 | Nakajima |
| 5,310,527 A | 5/1994 | Romanauskas et al. |

(Continued)

FOREIGN PATENT DOCUMENTS

| DE | 200 02 188 | 6/2000 |
| EP | 0 158 463 | 10/1985 |

(Continued)

OTHER PUBLICATIONS

International Search Report of Mar. 29, 2012.

(Continued)

*Primary Examiner* — John Kim
(74) *Attorney, Agent, or Firm* — Gerald E. Hespos; Michael J. Porco; Matthew T. Hespos

(57) ABSTRACT

A filtration container for concentration of macromolecules is insertable into a filtrate recovery tube (5) and has an upper portion (2), a central portion (3) axially adjoining the upper portion (2), and a lower portion (4) axially adjoining the central portion (3). The upper portion (3) forms a hollow-cylindrical sample container (7) with an inlet opening (9) on its upper end face (8). The downwardly tapering central portion (3) has a filtration chamber (11) with two mutually opposed main walls (12, 13) running down toward one another. At least one of the main walls (12, 13) has a filter window (16) for receiving a planar membrane filter (17). The lower portion (4) forms a retentate chamber (21) adjoining the lower edge (18) of the filter window (16) A base (26) of the retentate chamber (21) slopes down on one side laterally.

9 Claims, 4 Drawing Sheets

(56) References Cited

U.S. PATENT DOCUMENTS

| | | |
|---|---|---|
| 5,647,990 A | 7/1997 | Vassarotti |
| 6,156,190 A | 12/2000 | Xia et al. |
| 6,719,896 B1 | 4/2004 | Clark |
| 6,837,995 B1 | 1/2005 | Vassarotti et al. |
| 2009/0078638 A1 | 3/2009 | Bonhomme et al. |

FOREIGN PATENT DOCUMENTS

| | | |
|---|---|---|
| EP | 0 651 675 | 10/1997 |
| JP | 62-011564 | 1/1987 |

OTHER PUBLICATIONS

Translation International Preliminary Report on Patentability, (Aug. 2013).

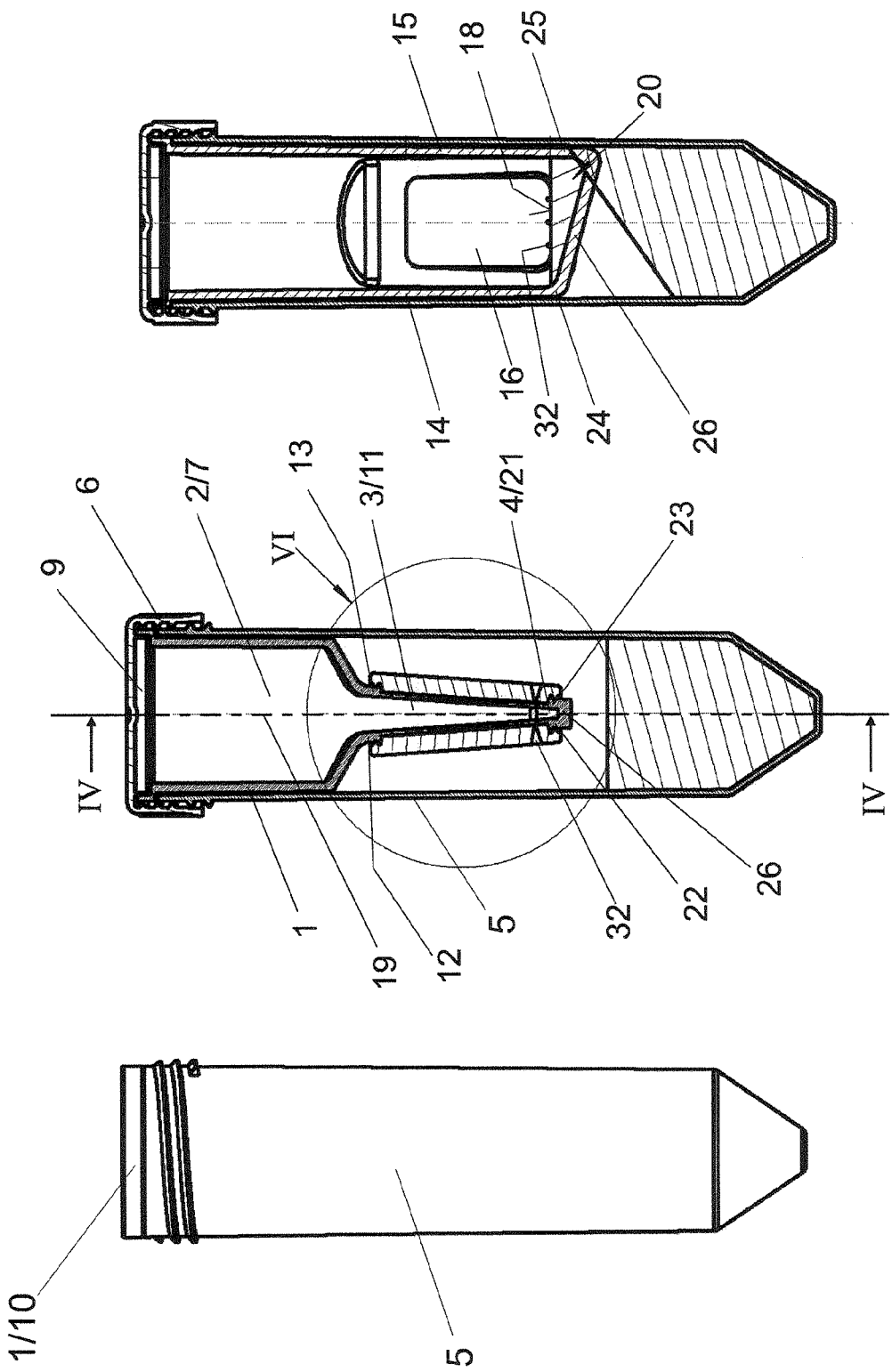

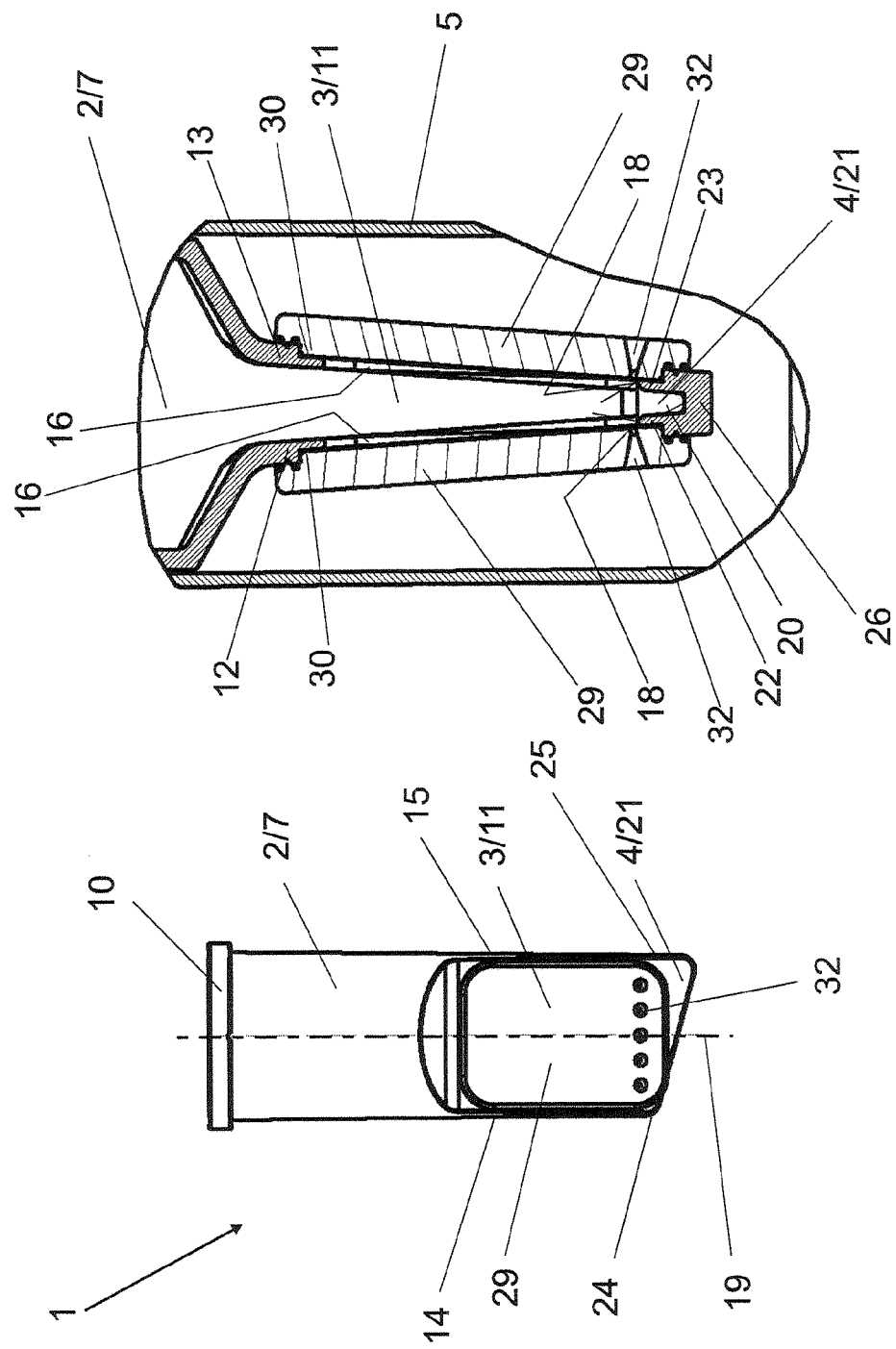

FILTRATION CONTAINER

BACKGROUND

1. Field of the Invention

The invention relates to a filtration container, in particular for concentration of macromolecules, said filtration container being insertable into a filtrate recovery tube and comprising an upper portion, a central portion axially adjoining the upper portion, and a lower portion axially adjoining the central portion, of which
- the upper portion forms a sample container, which is hollow-cylindrical and has an inlet opening on its upper end face,
- the downwardly tapering central portion a filtration chamber, which has two mutually opposed main walls running downwardly towards one another and also two gusset-like connection walls connecting said main walls at the lateral edges thereof, at least one of the main walls having a filter window for receiving a planar membrane filter, and
- the lower portion forms a retentate chamber adjoining the lower edge of the filter window, the defining main walls and connection walls of said retentate chamber being planar extensions of the main walls and connection walls of the central portion.

2. Description of the Related Art

Macromolecules, in particular protein samples, are concentrated in a volume range from 500 µl to 20 ml in filtration containers, which are inserted into a filtrate recovery tube and are concentrated in centrifugal units via the method of ultrafiltration. In the case of ultrafiltration, it is normal to provide a retentate chamber in the form of what is known as a dead stop pocket in the filtration containers, this being intended to prevent the sample from running dry. Here, the concentrated sample is collected in the dead volume formed by the retentate chamber and is recovered again by pipetting.

The recovery of the entire concentrate is very critical, since the volume is very small. This means that losses of just a few microliters lead to high percentage losses of the final yields.

EP 0 651 675 B1 discloses a filtration container for concentration of macromolecules, which, in conjunction with a filtrate recovery tube and a microconcentrating device for concentrating macromolecules from a solution by rotation of the microconcentrating device in a centrifuge, collects the concentrated macromolecules in a retentate container. The known filtration container consists of an upper portion, a central portion axially adjoining the upper portion, and an axially adjoining lower portion. Here, the upper portion forms a sample container, which is hollow-cylindrical, and the downwardly tapering central portion forms a filtration chamber, which has two mutually opposed main walls running downwardly towards one another and also two connection walls connecting said main walls at the lateral edges thereof. One of the main walls here forms a filter window for receiving a flat membrane filter. The adjoining lower portion forms a retentate chamber, which adjoins the lower edge of the filter window and of which the defining main walls and connection walls are planar extensions of the main walls and connection walls of the central portion.

Although this known device has proven its worth in principle, it has been found that complete sample recovery is very difficult.

Furthermore, a filtration container for centrifugal concentration of macromolecules is known from JP 62-11564 A1. A substantially hollow-cylindrical container has a cylindrical insert that divides the container in the longitudinal direction and has a sealing collar. Here, a beveled attachment is arranged above the collar and its entry opening is covered by a filter membrane, which therefore rises by an angle between 25 and 45°. Here, an annular retentate chamber is formed between the attachment and the surrounding container wall, and the retentate is collected in said retentate chamber.

With this device too, a complete and defined sample recovery has proven to be very difficult.

The object of the present invention is therefore to specify a filtration container that has a retentate chamber and that enables practically complete sample recovery.

SUMMARY OF THE INVENTION

This object is achieved by forming the base of the retentate chamber to slope downwardly on one side laterally, such that a first connection wall of the retentate chamber is shorter than the mutually opposed second connection wall.

Due to the base of the retentate chamber sloping downwardly in an inclined manner, it is ensured that a practically complete sample recovery of the sample or of the retentate is enabled as the retentate is pipetted from the retentate chamber. The pipette has to be arranged merely with its tip adjacent to the second connection wall at the base of the retentate chamber.

In accordance with a preferred embodiment of the invention, the main walls running towards one another are planar, the connection walls being extensions of the hollow-cylindrical wall of the upper portion. Due to the main walls running towards one another, the creation or the formation of a retentate chamber with a small volume is favored.

In accordance with a further preferred embodiment of the invention, the base is planar and has a rounded transition to the connection walls. Due to the rounded transition, runoff of the retentate towards the deepest point of the retentate container is favored and complete suction with a pipette is improved.

In accordance with a further preferred embodiment of the invention, the planar membrane filter on its outer face facing away from the filtration chamber has a filter cover, which, adjacently above the lower edge of the filter window, has a plurality of filtrate channels arranged side by side.

In accordance with a further preferred embodiment of the invention, the filtrate channels are conically widened towards their outer face facing away from the membrane filter. Here, the filtrate channels have relatively small openings towards the membrane filter, which form a defined boundary with respect to the filtrate chamber, the enlarged outlet openings of said filtrate channels favoring the flow of filtrate into the filtrate recovery tube.

In accordance with a further preferred embodiment of the invention, at least the retentate chamber is formed from a chemically inert material, in particular from the polymer polystyrene. Polystyrene has the advantage that it is chemically inert and has no protein-binding properties. Due to the design according to the invention, the collection of the concentrated sample or of the retentate in a very small volume space, which is additionally chemically inert, is made possible.

In accordance with a further preferred embodiment of the invention, the base of the retentate chamber is inclined relative to the horizontal lower edge of the filter window by an angle of inclination between more than 5° and 30°, preferably by approximately 15°.

Further details of the invention will emerge from the following detailed description and the accompanying drawings, in which preferred embodiments of the invention are illustrated by way of example.

BRIEF DESCRIPTION OF THE DRAWINGS

FIG. 2 shows a side view of the filter recovery tube from FIG. 1.

FIG. 3 shows a side view in section of the filtration container from FIG. 1, inserted into the filtrate recovery tube from FIG. 1, and of a fitted closure cap.

FIG. 4 shows a side view in section of the filtrate recovery tube from FIG. 3 with a filtration container and closure cap, taken along the line of section IV-IV.

FIG. 5 shows a side view of the filtration container from FIG. 4.

FIG. 6 shows an enlarged illustration of the detail VI from FIG. 3.

DETAILED DESCRIPTION OF THE PREFERRED EMBODIMENTS

Figure 1:
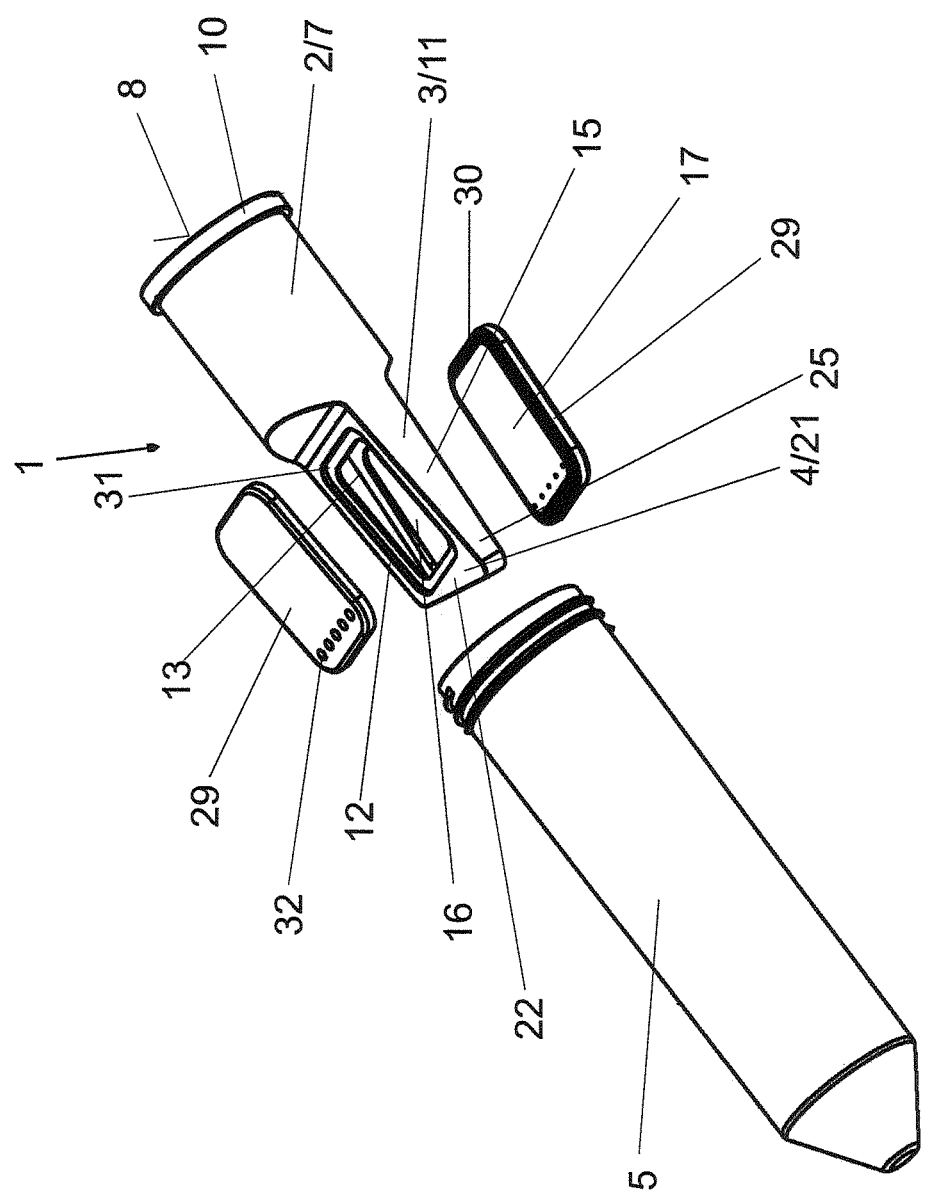
FIG. 1 shows a three-dimensional illustration of a filtration container with a filtrate recovery tube in the form of an exploded illustration without closure cap of the filtrate recovery tube.
Figure 9:
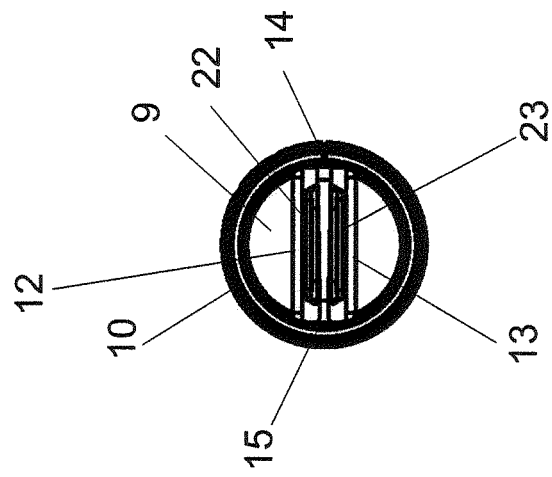
FIG. 9 shows a plan view of the filtration container from FIG. 7 from direction IX.
Figure 8:
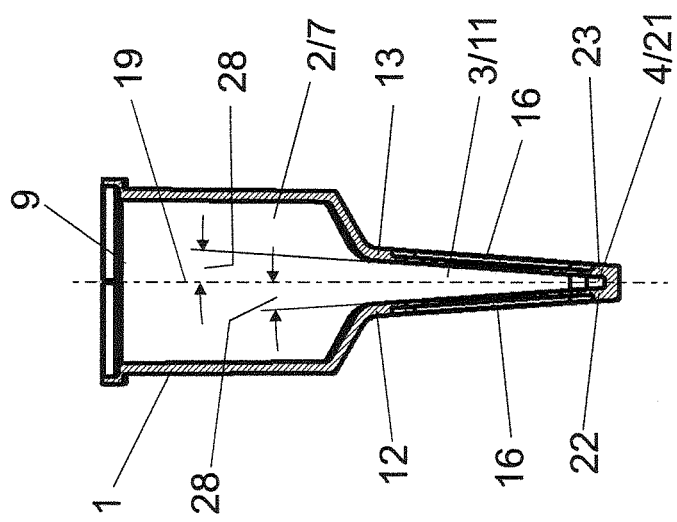
FIG. 8 shows a side view of the filtration container from FIG. 7, taken along the line of section VIII-VIII.
Figure 7:
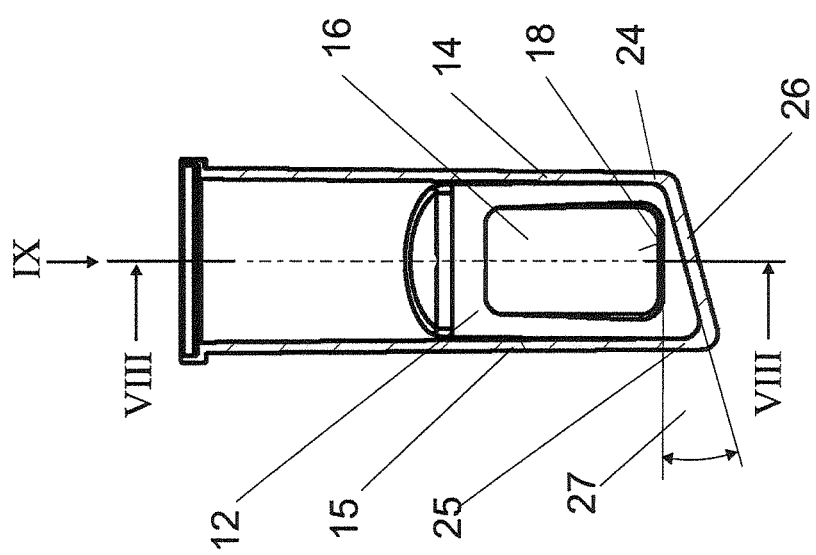
FIG. 7 shows a rear view in section of the filtration container from FIG. 5 without membrane filter and filter cover.

A filtration container 1 basically consists of an upper portion 2, a central portion 3, and from a lower portion 4.

The filtration container 1 can be inserted into a filtrate recovery tube 5, which can be closed by a closure cap 6. The upper portion 2 forms a sample container 7, which is hollow-cylindrical and has an inlet opening 9 on its upper end face 8.

At its upper end, the upper portion 2 has a peripheral bead 10, which is used as a stop relative to the filtrate recovery tube 5. At its lower end facing away from the upper end face 8, the upper portion 2 transitions into the central portion 3. The central portion 3 tapers downwardly in the vertical direction and forms a filtration chamber 11, which has two mutually opposed main walls 12, 13 running downwardly towards one another and also two gusset-like connection walls 14, 15 connecting said main walls at the lateral edges thereof. A filter window 16 for receiving a planar membrane filter 17 is arranged in each of the connection walls 14, 15. The filter windows 16 each have a lower edge 18, which runs transversely to the longitudinal axis 19 of the filtration container 1 and which is adjoined downwardly in the vertical direction by the lower portion 4. The lower portion 4 forms a retentate chamber 21, of which the defining main walls 22, 23 with connection walls 24, 25 are extensions of the main walls 12, 13 and of the connection walls 14, 15 of the filtration chamber 11. The retentate chamber 21 is defined downwardly in the vertical direction by a base 26. The base 26 of the retentate chamber 21 is formed so as to slope downwardly on one side laterally, such that the first connection wall 24 of the retentate chamber 21 is shorter than the opposed second connection wall 25. The planar base 26 is inclined relative to the horizontal lower edge 18 of the filter window 16 by an angle of inclination 27 of approximately 15°. The main walls 12, 13 running towards one another each form an angle of inclination 28 relative to the longitudinal axis 19 of approximately 4°.

To receive the concentrated sample, the retentate chamber forms a retentate volume 20 (dead space) below the lower edge 18.

The membrane filters 17, which close the filter windows in a sealed manner and which are flat, are arranged in the filter windows 16. The membrane filters 17 are each covered on their outer face facing away from the filtration chamber 11 by a filter cover 29 connected to the main walls 12, 13. The filter cover 29 engages here via an inner shoulder 30 in a peripheral recess 31 in the filter window 16. The filter cover 29 has a plurality of filtrate channels 32 arranged side by side adjacently above the lower edge 18 of the filter window 16. The filtrate channels 32 are conically widened towards their outer face facing away from the membrane filter 17.

The filtration container 1 is formed from the polymer polystyrene.

The invention claimed is:
1. A filtration container (1) for concentration of macromolecules, said filtration container being insertable into a filtrate recovery tube (5) and comprising:
an upper portion (2) forming a hollow-cylindrical sample container (7) generated about a longitudinal axis (19), the upper portion (2) having an upper end face (8) and an inlet opening (9) on the upper end face (8),
a downwardly tapering central portion (3) axially adjoining the upper portion (2) and forming a filtration chamber (11) with planar first and second main walls (12, 13) extending down from the upper portion and converging towards one another at opposite sides of a diametrical plane that contains the longitudinal axis (19) of the upper portion (2) and first and second gusset-like connection walls (14, 15) connecting said main walls (12, 13) at lateral edges thereof, first and second filter windows (16) formed respectively in the first and second main walls (12, 13) for receiving planar membrane filters (17), each of the filter windows (16) having a lower edge (18) aligned transverse to the longitudinal axis (19), and
a lower portion (4) axially adjoining the central portion (3) and forming a retentate chamber (21) adjoining the lower edges (18) of the filter windows (16), the retentate chamber (21) having lower portion main walls (22, 23) that are planar extensions of the main walls (12, 13) of the central portion (3), a first lower portion connection wall (24) defining a curved extension of the first connection wall (14) of the central portion (3) and being at a position substantially aligned with the lower edges (18) of the filter windows (16) in a direction transverse to the longitudinal axis (19), a second lower portion connection wall (25) defining an extension of the second connection wall (15) of the central portion (3) extending to a position lower than the lower edges (18) of the filter windows (16) in the direction transverse to the longitudinal axis (19), the retentate chamber (21) having a base (26) formed to slope down from the first lower portion connection wall (24) at a position substantially aligned with the lower edges (18) of the filter windows (16) in the direction transverse to the longitudinal axis (19) to a lower end of the second lower portion connection wall (25), wherein
each of the planar membrane filters (17) has an outer face facing away from the filtration chamber (11), the outer face of each of the membrane filters (17) having a filter cover (29) with a plurality of filter channels (32) extend- ing transverse to the respective main walls (12, 13) and arranged side by side at positions adjacent to and above the lower edge (18) of the respective filter window (16).

2. The filtration container of claim 1, wherein the connection walls (14, 15) of the central portion (3) are extensions of the hollow-cylindrical sample container (7) formed by the upper portion (2).

3. The filtration container of claim 1, wherein the base (26) is planar and has a rounded transition to the connection walls (24, 25) of the retentate chamber (21).

4. The filtration container of claim 1, wherein: the filtrate channels (32) are conically widened towards their outer face facing away from the membrane filter (17).

5. The filtration container of claim 1, wherein at least the retentate chamber (21) is formed from a chemically inert material.

6. The filtration container of claim 5, wherein the retentate chamber (21) is formed from polystyrene.

7. The filtration container of claim 1, wherein the base (26) of the retentate chamber (21) is inclined relative to the lower edges (18) of the filter windows (16) by an angle of inclination (27) between 5° and 30°.

8. The filtration container of claim 7, wherein the angle of inclination (27) is approximately 15°.

9. The filtration container of claim 1, wherein the first and second main walls (12, 13) of the central portion (3) converge toward one another to define an angle of approximately 4° to the longitudinal axis (19).

\* \* \* \* \*